of Germany
United States Patent [19]

Spaeth

[11] 4,297,579
[45] Oct. 27, 1981

[54] BI-FREQUENCY INFRARED SPECTROMETER

[75] Inventor: Tilman P. Spaeth, Sipplingen, Fed. Rep. of Germany

[73] Assignee: Bodenseewerk Geosystem GmbH, Überlingen, Fed. Rep. of Germany

[21] Appl. No.: 156,505

[22] Filed: Jun. 4, 1980

[30] Foreign Application Priority Data

Jun. 15, 1979 [DE]  Fed. Rep. of Germany ....... 2924131
Jun. 15, 1979 [DE]  Fed. Rep. of Germany ....... 2924132
Jun. 15, 1979 [EP]  European Pat. Off. .......... 79101976

[51] Int. Cl.³ ........................................... G01N 21/26
[52] U.S. Cl. ................... 250/343; 250/345; 356/434; 356/436
[58] Field of Search ............. 250/336, 338, 343, 344, 250/345, 346; 356/432, 433, 434, 436, 51

[56] References Cited

U.S. PATENT DOCUMENTS 4,205,913  6/1980  Ehrfeld et al. ................. 250/343 X

*Primary Examiner*—Davis L. Willis
*Attorney, Agent, or Firm*—Darbo & Vandenburgh

[57] ABSTRACT

In a bi-frequency infrared spectrometer having a filter wheel rotating in the path of rays, which filter wheel carries two semicircular filters transparent in different spectral ranges, the influence of the radiation from the filters themselves is eliminated in that the filter wheel has an opaque backplate on the side facing the light source, said backplate having one aperture in the area of each filter, which aperture passes through the path of rays. In this way the detector "sees", at first, only the filter with the radiation emanating from the filter itself, and is subsequently exposed to the measuring beam emanating from the light source and passing through the sample cell, when the aperture is being moved through the path of rays. A clamp circuit keeps the output signal zero until shortly before the aperture passes through the measuring beam. The detector signal is integrated by an integrator during a measuring time interval and a reference time interval. In order to eliminate the infuences of inertia and memory effects of the integrator, the detector signal is integrated with reversed sign during a certain time interval before each reference time interval and each measuring time interval. The logarithms of the output signals of the integrator are formed and are transferred to a memory after each reference time interval and each measuring time interval. The integrator is then reset to zero. The difference of the stored signals should then be a measure of the concentration of an element sought, the absorption band of which coincides with the transmission range of one of the filters. In order to get a linear relation between the output signal obtained and the concentration, even if there are deviations from Beer's Law or the measurement is affected by the radiation from instrument parts themselves or the different transmissivities of the filters, adjustable corrective voltages are applied to the integrator, and the signal is applied to the integrator through different resistances during the measuring time interval and during the reference time interval. A filter having a transfer function inverse to the transfer function of the detector is connected to receive the output of the detector.

13 Claims, 6 Drawing Figures

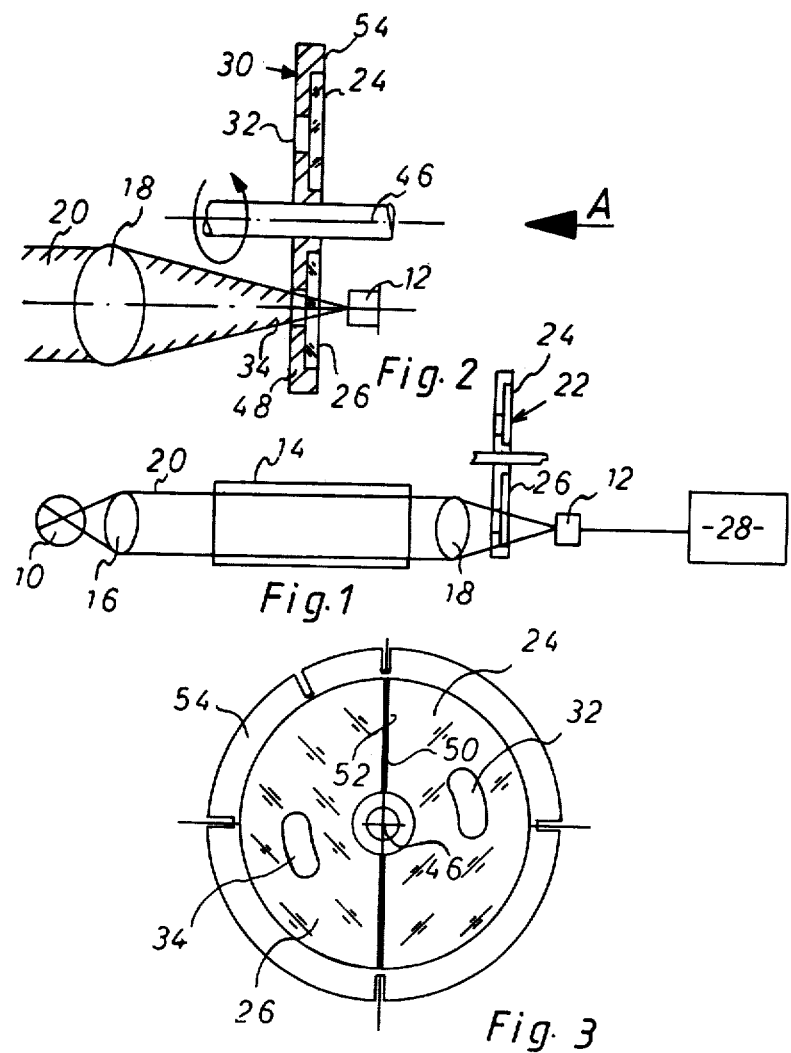

BI-FREQUENCY INFRARED SPECTROMETER

STATEMENT OF PRIOR ART

Bi-frequency infrared spectrometers are known. They comprise a radiation source, which emits infrared radiation, a detector responding to infrared radiation, and a sample cell between radiation source and detector. An optical system passes a beam of radiation emanating from the radiation source through the cell and onto the detector. A filter device comprises two filters, which are transparent in different wavelength ranges in the infrared and which are arranged to be moved alternatingly into the path of the beam of radiation. A first time interval (reference window), during which one of the filters mentioned above is in the path of the beam, and a second time interval (measuring window), during which the other filter is in the area of the measuring beam, are defined. A signal evaluation circuit comprises a reset integrator, which integrates the detector signal during a reference time interval located within the reference window and a measuring time interval located within the measuring window. After each reference time interval and after each measuring time interval, the output signal of the integrator is transferred to a respective memory circuit, the integrator being subsequently, i.e. after each such transfer, reset to zero.

Such Bi-frequency infrared spectrometers serve, for example, for the determination of the concentration of an absorbing gas in a cell. The wavelength passed by the filter coincides with an absorption band of a compound sought, while the other wavelength is located outside the absorption band and permits taking into account the background absorption, variations of the light source brightness or the sensitivity of the detector. With some substances, for example uranium hexafluoride, the essential absorption band, which can be utilized for a measurement, is located in the medium to long wavelength infrared. Therefore one of the filters has to be transparent in this range, and the detector has to respond to such radiation.

The detectors of this type are subjected to inertia and memory. This means that the output signal of the detector follows an increase of radiation energy only with delay, while, on the other hand, the output signal decays with delay, after the radiation energy has dropped. Due to these characteristics of the detector, the signals resulting from the radiations of the two wavelengths overlap. Superposed are spurious signals which are due to variations of ambient temperature. German Offenlegungsschrift No. 27 27 976 discloses a signal evaluation circuit for a bi-frequency photometer of the type described hereinbefore, wherein the detector signal is integrated by an integrator during predetermined reference and measuring time intervals, each of which is associated with one of two alternating measured quantities, i.e. beam intensities.

Also measures are taken to separate the overlapping signals resulting from the two alternating measuring quantities. These measures are, however, effective only at one point of the measuring range, i.e. range of intensity ratios in the reference and measuring windows, while in the remainder of the measuring range there is no clear separation of the signals. This makes the prior art instrument inappropriate for many applications. With some applications, for example, the bi-frequency photometer is required to still provide an accurate measurement, even if the intensity of the beam in the measuring window is as low as 3 percent of the intensity of the beam in the reference window. Under such conditions of an incomplete separation of the signal components, if a percentage of the intense beam from the reference window affects the signal of the beam in the measuring window, considerable measuring errors will result.

BACKGROUND AND SUMMARY OF THE INVENTION

One problem which presents itself with measurements in the medium to long wavelength infrared is the radiation emanating from the various components of the instrument themselves. An essential contribution to such radiation is due to radiation from the filters themselves. This radiation is also modulated with the filter alternation frequency. It is not restricted to the narrow transmission range of the filters, and as the detector generally responds non-specifically to the total radiation, this spurious signal caused by the radiation of the filters themselves can result in considerable falsification of the measuring signal.

It is an object of the invention to provide a bi-frequency infrared spectrometer wherein the influence of the radiation of the filters themselves is eliminated.

A further object of the invention is to provide a signal evaluation circuit which permits clear separation of alternating measured quantities, the waveforms of which overlap partially.

A further object of the invention is to provide a signal evaluation circuit for a measuring instrument operating in accordance with the bi-frequency method to determine the concentration of a substance in a sample from extinction such that, on one hand, the influence of the radiation and of the different transmissivities of the filters can be compensated for, and, on the other hand, an output signal, which is a linear function of the concentration of the sought substance in the sample is obtained even with deviation from Beer's Law.

In one embodiment of the invention the filters are attached to a carrier so as to face the detector. The carrier has an aperture in the area of each filter. The dimensions of these apertures are smaller than those of the filters. The carrier is arranged to pass with its apertures through the path of the beam of radiation. The beam of radiation alternatingly falls through one and the other aperture and filter onto the detector and is covered, prior to the passage of the beam through an aperture, by the carrier arranged on the side facing the radiation source, while portions of the filter beside the aperture are in said path. A clamp circuit is provided, which is connected to clamp the detector signal to a baseline during the reference window and during the measuring window until shortly before the reference time interval and the measuring time interval, respectively, begin.

With such an arrangement, the detector "sees", at first, the filter surface, which is shielded by the carrier from the radiation source. Therefore the detector signal represents the radiation from the filter itself. This detector signal is clamped to a baseline by the clamp circuit. During the subsequent reference or measuring time intervals, only the variation of the detector signal relative to the detector signal caused by the radiation of the filter will be integrated. Thus a measured value independent of this filter radiation will be obtained.

According to another aspect of the invention, the output signal from the clamp circuit is applied to the integrator directly through a first switch controlled by the programmer, and inverted through a second switch also controlled by the programmer. One switch is closed by the programmer during each reference and measuring time interval, and the other switch is closed during compensation time intervals defined before each reference and measuring time interval. The clamp circuit is arranged to be actuated by the programmer to clamp the detector signal to a baseline before each reference, measuring and compensation time interval. The programmer is arranged to apply the output signal of the integrator or a function, such as the logarithm, of this signal to one memory circuit each, after each reference time interval and after each measuring time interval. The integrator is arranged to be reset to zero by the programmer after each application of the output signal to one of the memory circuits.

The programmer defines a time interval during which one measuring quantity is predominate, and a second time interval, in which the other measuring quantity is predominate. Herein these two time intervals will be called "reference window" and "measuring window". Each measuring quantity is measured by integrating the signal during a reference time interval, which is located within the reference window, and during a measuring time interval, which is located within the measuring window. In the reference window, however, there will be signal components which result from the measuring quantity measured within the measuring window and vice versa. For this reason, prior to the measurement of one of the measuring quantities by integration during the reference time interval, the signal is integrated during a compensation time interval. There is also an integration during a compensation time interval before the measuring time interval. Before each integration interval the detector signal is "clamped" to a baseline by a clamp circuit. The shape of the signal waveform at the detector with a predetermined, for example triangular, waveform of the measuring quantities has always the same character independent of the amplitudes of the measuring quantities. Therefore the integral of the detector signal formed during the compensation time interval has a fixed ratio to the integral, formed during the measuring or reference time interval, of the signal component resulting from the respective other measuring quantity. When, therefore, the gain of application of the detector signal during the compensation time interval and the length of the compensation time interval are selected properly, the influence of one measuring quantity on the measurement of the respective other one and vice versa is eliminated by the integrations carried out with opposite signs.

The signal waveforms at the detector with, for example, triangular waveform of the measuring quantity acting on the detector are rather irregular with conventional detectors, and are different from detector to detector with the same character. Therefore the application of the signals to the integrator during the various time intervals has to be adjusted individually for each detector.

According to a further modification of the invention, provision is made that a filter is connected to receive the output signal of the detector, the transfer function of said filter being inverse to the transfer function of the detector.

Also with such a filter alone separation of the signals might be achieved. If such a filter were used alone, accurate matching of the filter to the characteristics of the respective detector would also be required.

It has, however, been found that with the combination of the circuit described in the beginning with a series connected filter the transfer function of which is inverse to the transfer function of the detector, practically no adjustment for matching to the specific parameters of the detector is required.

According to a further aspect of the invention an adjustable corrective voltage is superposed on the detector signal at the input of the integrator during the reference time interval and during the measuring time interval. The detector signal is applied to the input of the integrator through two different resistances controlled by a controlled switch. At least one of the above mentioned resistances is adjustable. The controlled switch is controlled by the programmer such that one resistance is effective during the reference time interval, and the other resistance is effective during the measuring time interval. The corrective voltages and the adjustable resistance are adjusted such that a substantially linear relation exists between output signal and concentration taking into account the radiation of components of the instrument itself and the different transmissivities of the filter as well as deviations of the extinction from Beer's Law.

By superposing the adjustable corrective voltages to the reference and measuring signals at the input of the integrator, curvature of the extinction-concentration characteristic can be compensated for, which curvature occurs deviating from Beer's Law. An offset of the zero point is compensated for by varying the ratio of the signals applied from the detector to the input of the integrator. Such variation of the ratio by a constant factor results in a term of a sum after formation of the logarithm, and this term can be selected to ensure that the output signal as function of concentration passes through the coordinate origin, thus the output signal becomes zero, when the concentration is zero.

The same corrective voltages may serve to compensate for the influence of the radiation of components of the instrument itself. The linearization described hereinbefore is achieved by "miss-compensation" of these instrument radiation influences.

In similar manner the adjustment of the adjustable resistance through which one of the signals is applied to the integrator may be used to take the "filter factor" into account. Also here a "miss-compensation" can ensure that the linearized concentration-output signal characteristic passes through the coordinate origin.

An embodiment of the invention is described in greater detail hereinbelow with reference to the accompanying drawings.

BRIEF DESCRIPTION OF THE DRAWINGS

FIG. 1 shows schematically a bi-frequency infrared spectrometer.

FIG. 2 shows a side elevation of the filter device in the bi-frequency infrared spectrometer of FIG. 1.

FIG. 3 is a view in the direction of the arrow A of FIG. 2.

DESCRIPTION OF SPECIFIC EMBODIMENT

Figure 4:
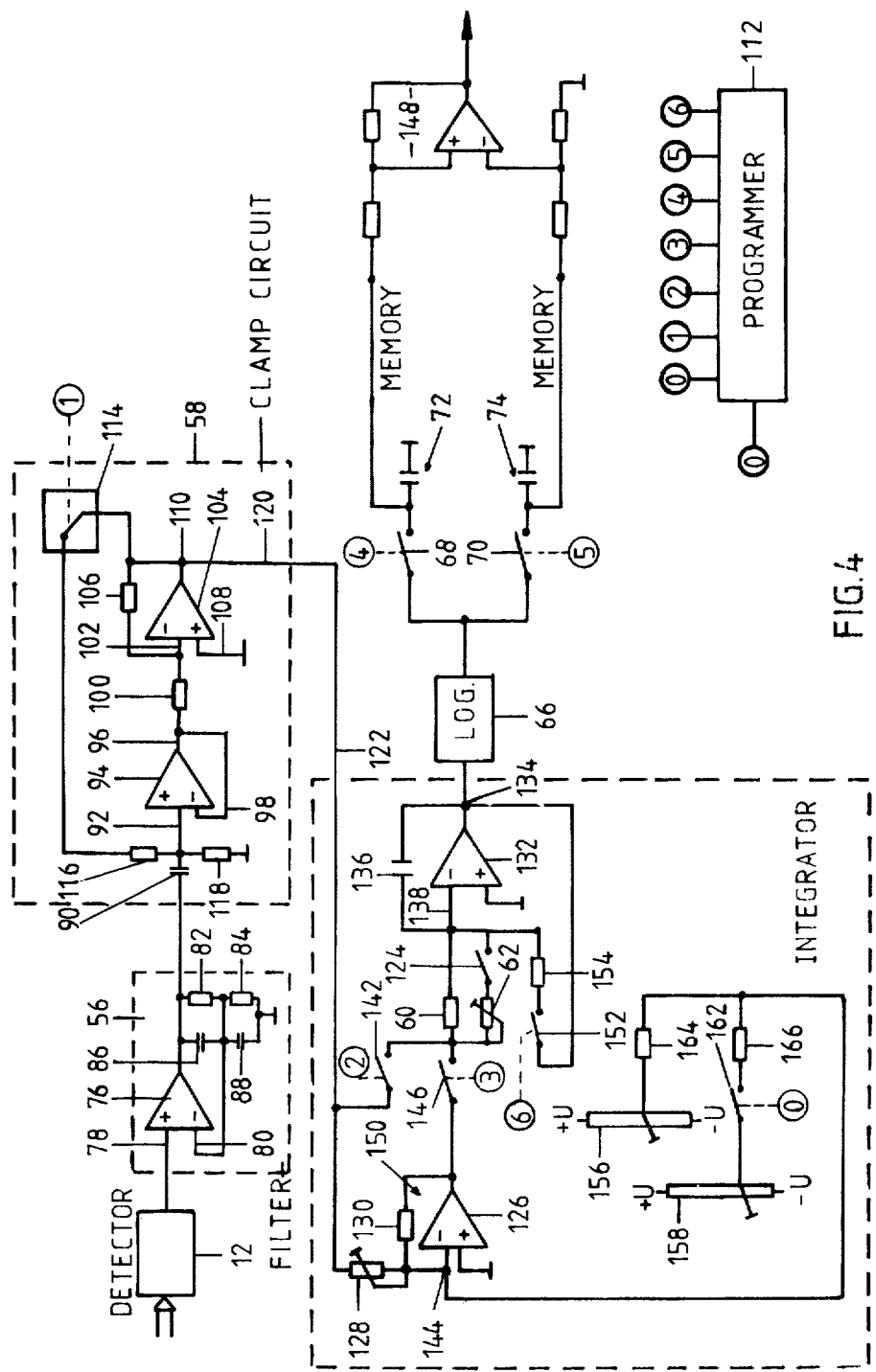
FIG. 4 is a simplified wiring diagram of the signal evaluation circuit.

The bi-frequency infrared spectrometer comprises a radiation source 10, which emits infrared radiation, a detector 12 responding to infrared radiation, a sample cell 14 between radiation source and detector, and an optical system, illustrated by lenses 16 and 18, which passes a beam 20 of radiation emanating from the radiation source 10 through the cell 14 and onto the detector 12. Furthermore a filter device 22 is provided having two filters 24,26, which are transparent in two different wavelength ranges in the infrared range. The two filters 24,26 are arranged to be moved alternatingly into the path of the beam 20 of radiation. The detector signal from the detector 12 is applied to a signal evaluation circuit 28 still to be described.

As can be seen from FIGS. 2 and 3, the filters 24,26 are attached to a carrier 30, such as to face the detector. The carrier 30 has apertures 32 and 34, respectively, in the area of each filter 24,26. The dimensions of the apertures 32 and 34 are smaller than those of the filters 24 and 26, respectively. The carrier 30 is arranged to pass with its apertures 32,34 through the path of the beam 20 of radiation. The beam 20 passes alternatingly through one and the other aperture and filter onto the detector 12. Prior to each passage of the beam 20 through an aperture, the beam 20 is covered by the carrier arranged on the side of the radiation source 10, while portions of the filters 24 or 26 beside the aperture 32 or 34, respectively, are in the path of rays of the beam 20. Thus before the beam 20 falls on the detector 12, the detector 12 receives, at first, only radiation emanating from the filters 24 or 26 themselves as well as the stray radiation reflected by the filters.

As can be seen in detail from FIGS. 2 and 3, the filter device comprises a disc 48 rotating about the axis of rotation 46 and having the two apertures centrosymmetrical with respect to the axis of rotation 46. Each aperture 32 and 34 is an arcuate slot curved about the axis of rotation 46. Each aperture 32 and 34 is covered, on the side facing the detector, by one of the filters 24 and 26, respectively, which extend laterally beyond the aperture 24 or 26. Each filter 24 and 26 is a substantially semicircular filter plate, which is attached to the disc and has a substantially straight edge, for example 50, along a diameter. The edge 50 of one filter 24 is closely adjacent the edge 52 of the other filter 26. On the side facing the detector, the disc 48 has a projecting collar 54 concentric with the axis of rotation 46. The two semicircular filter plates 24 and 26, which together form a full circle, are centered in this projecting collar.

The signal evaluation circuit 28 comprises a filter 56 connected to receive the output signal from the detector 12. The transfer function of this filter 56 is inverse to the transfer function of the detector 12. The detector signal thus filtered is applied to a clamp circuit 58. The output signal of the clamp circuit 58 is applied to a reset integrator 64. The output signal of the integrator 64 is applied to a logarithm former 66. The logarithm of the integrator signal can be applied to memory circuits 72 and 74 through switches 68 and 70.

The filter 56, which in the embodiment illustrated is designed for a pyroelectric detector responding to infrared radiation, comprises an operational amplifier 76 having a non-inverting input 78 and an inverting input 80. The detector signal is applied to the non-inverting input 78 of the operational amplifier 76. A voltage divider, which comprises two series connected complex impedances, is connected to the output of the operational amplifier 76. Each of these complex impedances comprises an ohmic resistor 82 and 84, respectively, and a capacitor 86 and 88, respectively. The voltage tapped between the complex resistances is applied to the inverting input 80 of the operational amplifier 76.

The clamp circuit 58 comprises a capacitor 90 through which the output of the filter 56 is connected to the non-inverting input 92 of an operational amplifier 94 acting as impedance transformer, the output 96 of the operational amplifier 94 being connected to the inverting input 98. The output 96 of the operational amplifier 94 is connected to the inverting input 102 of an operational amplifier 104 through a resistor 100. The output of the operational amplifier 104 is connected to the inverting input 102 through a further resistor 106. The non-inverting input 108 of the operational amplifier 104 is grounded. In this way the signal received at the first operational amplifier 94 is amplified. The output 110 of the second operational amplifier 104 can be connected to the input 92 of the first operational amplifier 94 through a switch 114 controlled by a programmer in a manner still to be described, and through a voltage divider comprising resistors 116 and 118.

Upon closing of switch 114, the capacitor 90 will be re-charged by the amplified voltage from the second operational amplifier 104, until the voltage at the first operational amplifier becomes zero. The output signal of the clamp circuit 58 is tapped from the output 110 of the second operational amplifier 104, as indicated by conductor 120.

The output signal of the clamp circuit 53 is applied to the input 122 of the integrator 64. The integrator 64 comprises an operational amplifier 132, the output 134 of which is connected to the inverting input 138 of the operational amplifier 132 through a capacitor 136. The non-inverting input 140 of the operational amplifier 132 is grounded. The inverting input 138 is connected directly to the input 122 through a switch 142 and is connected through a switch 146 to the output of an inverting amplifier 150, to which the output signal of the clamp circuit 58 is applied. The voltages applied through the switches 142 and 146 are connected to the operational amplifier 132 through a resistor 60, to which an adjustable resistor 62 and a switch 124 connected in series thereto are connected in parallel. A third switch 152 controlled by the programmer 112 and in series connection with a discharge resistor 154 shunts the capacitor 136 to reset the integrator 64.

The inverting amplifier 150 comprises an operational amplifier 126 the inverting input 144 of which is connected to the input 122 of the integrator 64 through an adjustable resistor 128 and to the output of the operational amplifier 126 through a resistor 130.

Furthermore adjustable corrective voltages are applied to the inverting input of the operational amplifier 126 and are superposed to the output signal of the clamp circuit 58. The adjustable corrective voltages are provided by potentiometers 156,158, which are connected between a potentional +U positive with respect to ground and a potentional −U negative with respect to ground. The slider of the potentiometer 156 is connected permanently to the inverting input 144 through a resistor 164, and the slider of the potentiometer 158 is connected to the inverting input 144 through a switch 162 and a resistor 166. The switch 162 is arranged to be closed by the programmer 112 synchronously with the measuring window.

The voltages stored in the memories 72 and 74 are applied to a differential amplifier 148, which provides an output signal representing the concentration of the sought substance in the sample.

Figure 5:
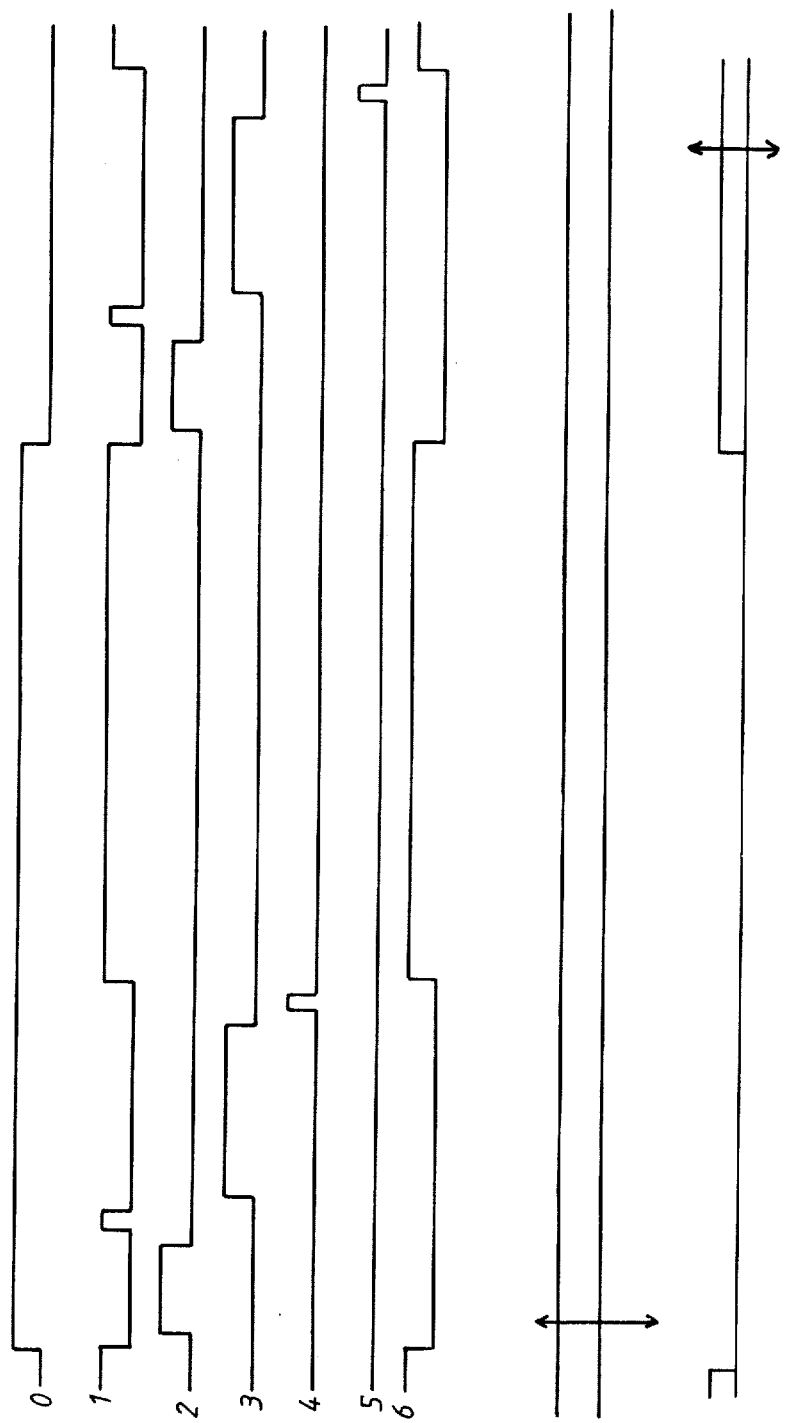
FIG. 5 shows the pulse diagram of the programmer for the signal evaluation circuit of FIG. 4.

The programmer 112 provides control signals "0", "1", "2", "3", "4", "5" and "6" which are illustrated in FIG. 5. Also illustrated in the last two lines of FIG. 5 are the voltages applied to the input 144 from potentiometer 156 and from potentiometer 158, respectively. The former voltage is continuous, while the latter voltage is applied through switch 162 during the measuring window only.

The switches are controlled by the various control signals in the manner indicated in FIG. 4: Switch 114 is controlled by signal "1". Switch 142 is controlled by signal ¢2". Switch 146 is controlled by signal "2". Switch 152 is controlled by signal "6". Switch 162 is controlled by signal "0". Switches 68 and 70 are controlled by signals "4" and "5", respectively.

The signals "0" to "6" are synchronized with the rotation of the filter device 22. In the simplest case the programmer could have cams, which rotate with the filter device and actuate one switch each. It is, however, also possible that the programmer comprises a counter, by which pulses from a counting pulse generator are counted at a fixed frequency. The counter may be reset with the rotational frequency of the filter device 22. The control signals may be generated by logic combination of the states of the counter stages in a manner known to the expert and therefore not described in detail.

The arrangement described operates as follows:

As can be seen from FIG. 5, the signal evaluation circuit 28 defines a first time interval "reference window" by the control signal "0", during which one of the filters 24 mentioned hereinbefore is in the path of the beam 20, and a second time interval "measuring window", during which the other filter 26 is in the path of the beam 20. During part of the reference window the beam 20 passes through the aperture 34. During part of the measuring window the beam passes through the aperture 32. The clamp circuit 58 keeps the signal applied to the input 122 of the integrator 64 zero, until shortly before this time interval, as illustrated by the control signal "1", whereby the baseline of this signal corresponds to the radiation emanating from or reflected by the filter 26. Then the integrator integrates the signal with reversed sign during a compensation time interval, which is given by control signal "2" (The clamp circuit 58 causes reversal of the sign of the detector signal). Subsequently the signal is again clamped to the baseline. Then the signal is integrated during the reference time interval in accordance with control signal "3". As can be seen from FIG. 4, the control signal "2" closes switch 142, which applies the signal from the input 122 directly to the input 138 of the operational amplifier 132, while switch 146 is closed by the control signal "3" and applies the signal from input 122 again inverted to the input 138 of the operational amplifier 132. Subsequently switch 68 is closed by the signal "4", and the logarithm of the output signal at output 134 of integrator 64, as provided by logarithm former 66, is applied to the memory 72. The integrator is reset to zero by the control signal "6". During the integration in the reference window, the output signal from the clamp circuit 58 is applied to the input 138 of the operational amplifier through a resistor 60. Simultaneously, the corrective voltage from potentiometer 156 is superposed. This serves to linearize the characteristic and to take the different filter transmissivities into account, as will be explained hereinbelow.

In similar manner the output signal of the clamp circuit 58 in the measuring window is, at first, clamped to a baseline, before the aperture 32 gets into the path of the beam 20. Thereby the influence of the radiation emanating from or reflected by the filter 24 itself is made zero. There will be again integration with reversed sign during a compensation time interval in accordance with signal "2", which closes switch 142. Subsequently switch 114 is closed again by control signal "1", and the output signal at the output 120 of the clamp circuit 58 is clamped to the baseline. Subsequently there is an integration again by closing switch 146 by control signal "3". Switch 70 is closed by control signal "5" and the logarithm of the output signal at the output 134 of the integrator 64, as provided by logarithm former 66, is transferred to the memory 74. Then the integrator 64 is reset to zero by the control signal "6", which closes the switch 152.

Here the output signal from the output 120 of the clamp circuit 58 or from the inverting amplifier 150, respectively, is applied to the input 138 of the operational amplifier 132 through the resistors 60 and 72 connected in parallel, after switch 124 has been closed by the control signal "0". The control signal "0" closes also siwtch 162, and thus adds an additional corrective voltage from potentiometer 158 at the input 144 of the operational amplifier 126.

By integration of the signals with reversed sign during the compensation time intervals, the influence of the detector 12 is compensated for, which influence results in overlapping of the signal, which are due to the light fluxes impinging on the detector 12 during the reference time interval and during the measuring time interval.

This will be explained in greater detail with reference to FIG. 6.

Figure 6:
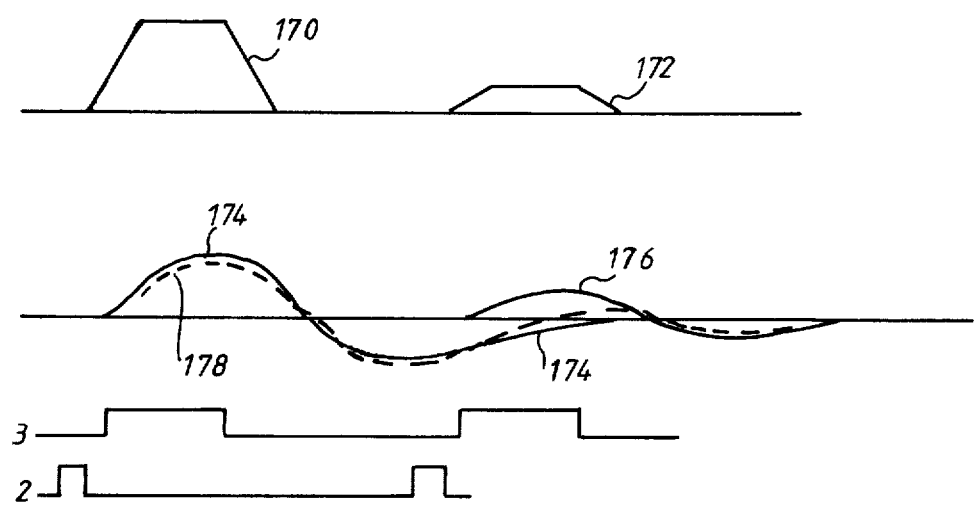
FIG. 6 shows typical waveforms at the detector.

In the first line of FIG. 6 the light flux falling on the detector 12 is plotted as a function of time, the radiation from the filters themselves being neglected for clarity. The light flux waveform 170 corresponds to the reference signal, i.e. the radiation from a wavelength range, in which the sample does not absorb. The light flux waveform 172 corresponds to the measuring signal, i.e. the radiation from the wavelength range, which coincides with an absorption band of the sample.

The second line shows the signal provided by the detector 12. The signal waveform 174 corresponds to the signal which would be caused by the light flux waveform 172 alone. The signal waveform 176 corresponds to the signal which would be caused by the light flux waveform 172 alone. It can be seen that the signal waveforms overlap and add up to a detector signal 178 shown in dashed lines.

In the lines therebelow, the signals "3" and "2" of FIG. 5 are illustrated again. The integration interval for the "negative" integration according to signal "2" is one quarter of the integration interval for the "positive" integration according to signal "3". To compensate for this, the positively integrated signal is applied through the inverting amplifier 150 with a gain of one quarter, the gain being adjusted by means of resistor 128.

The potentiometers 155 and 158 and the adjustable resistor 62 are set in such a manner that a substantially linear relation between output signal at the output of the differential amplifier 148 and concentration of the sought substance in the sample is achieved, taking the radiation from the components of the instrument itself and the different transmissivities of the filters as well as deviations of the extinction from Beer's Law into account.

In the present specification the term "switch" has been used, and mechanical switches are shown in FIG. 4 for clarity. These switches may, however, be electronic switches as will be apparent to those skilled in the art.

A bi-frequency infrared spectrometer is an instrument which, in cyclic succession, makes a measurement at a first wavelength, which coincides with the absorption band of a substance, and a measurement at a second wavelength, which is located outside this absorption band. The filter device may comprise more than two filters, whereby a plurality of substances can be measured simultaneously. Also-this possibility should be covered by the expression "bi-frequency infrared spectrometer".

I claim:

1. Signal processing circuit for the separation of overlapping signals, which are provided by a detector subjected to alternating measuring quantities and having inertia and/or memory,
   wherein the detector signal is integrated by an integrator during predetermined reference and measuring time intervals, each of which is associated with one of the alternating measuring quantities,
   characterized in that
   (a) a clamp circuit acting on the detector signal and controlled by a programmer is provided,
   (b) the output signal of the clamp circuit is applied to the integrator directly through a first switch controlled by the programmer, and inverted through a second switch also controlled by the programmer,
   (c) one switch is closed by the programmer during each reference and measuring time interval and the other switch is closed during compensation time intervals defined before each reference and measuring time interval,
   (d) the clamp circuit is arranged to be actuated by the programmer to clamp the detector signal to a baseline before each reference, measuring and compensation time interval,
   (e) the programmer is arranged to apply the output signal of the integrator or a function of this signal to one memory circuit each, after each reference time interval and after each measuring time interval, and
   (f) furthermore the integrator is arranged to be reset to zero by the programmer after each application of the output signal to one of the memory circuits.

2. Signal processing circuit as claimed in claim 1, characterized in that a filter is connected to receive the output signal of the detector, the transfer function of said filter being inverse to the transfer function of the detector.

3. Signal processing circuit as claimed in claim 2, for a pyroelectric detector responding to infrated radiation, characterized in that
   (a) the filter comprises an operational amplifier having non-inverting and inverting inputs,
   (b) the detector signal is applied to the non-inverting input of the operational amplifier,
   (c) a voltage divider is connected to the output of the operational amplifier and consists of the series connection of two complex impedances, each of these complex impedances being formed of an ohmic resistor and a capacitor connected in parallel thereto, and
   (d) the voltage tapped between the complex impedances is applied to the inverting input of the operational amplifier.

4. Signal processing circuit as claimed in claim 2, characterized in that
   (a) the clamp circuit comprises a capacitor through which the output of the filter is applied to the non-inverting input of a first operational amplifier acting as impedance transformer, the output of this operational amplifier being connected to the inverting input,
   (b) the output of the first operational amplifier is connected through a resistor to the inverting input of a second operational amplifier the outout of which is connected to the inverting input through a further resistor and the non-inverting input of which is grounded, whereby the signal obtained at the first operational amplifier is amplified,
   (c) the output of the second operational amplifier is arranged to be connected to the input of the first operational amplifier (60) through a switch controlled by the programmer and through a resistor, re-charging of the capacitor by the amplified voltage from the second operational amplifier being caused by closing the switch, until the voltage at the first operational amplifier becomes zero, the output signal of the clamp circuit being tapped from the output of the second operational amplifier.

5. Signal processing circuit as claimed in claim 4, characterized in that
   (a) the integrator comprises an operational amplifier the output of which is connected to the inverting input through a capacitor, and the non-inverting input of which is grounded,
   (b) the inverting input is connected directly to the output of the clamp circuit through the first switch and a first resistor and is connected through the second switch to the output of an inverting amplifier, to which the output signal of the clamp circuit is applied, and
   (c) a third switch controlled by the programmer in series with a discharge resistor shunts the capacitor to reset the integrator.

6. Signal processing circuit as claimed in claim 1, characterized in that a logarithm former is connected to receive the output signal from the integrator.

7. Signal processing circuit as claimed in claim 6, characterized in that the output signal from the logarithm former is transferred to a first analog memory circuit through a fourth switch and is transferred to a second analog memory circuit through a fifth switch, the fourth and fifth switches being controlled by the programmer to close for a short interval after each reference and measuring time interval.

8. Bi-frequency infrared spectrometer comprising:
   a radiation source, which emits infrared radiation,
   a detector responding to infrared radiation
   a sample cell between radiation source and detector,
   an optical system which passes a beam of radiation emanating from the radiation source through the cell onto the detector,
   a filter device having two filters transparent in two different wavelength ranges, of which at least one is in the infrared range, said filters being arranged to be moved alternatingly into the path of the beam of radiation, and a signal evaluation circuit, which comprises
means for defining a first time interval (reference window) during which the beam of radiation falls onto the detector through one of the aforementioned filters, and a second time interval (measuring window), during which the beam of radiation falls onto the detector through the other filter,
a reset integrator, which integrates the detector signal during a reference time interval located within the reference window and during a measuring time interval located within the measuring window,
memory circuits, to which the output signal of the integrator is transferred after each reference time interval and after each measuring time interval, the integrator being reset after each of said intervals, characterized in that
(a) the filters are attached to a carrier so as to face the detector, said carrier having an aperture in the area of each filter, the dimensions of said aperture being smaller than those of the filters,
(b) the carrier is arranged to pass with its apertures through the path of the beam of radiation, the beam of radiation alternatingly passing through one and the other aperture and filter onto the detector, and being covered, prior to each passage of the beam through an aperture, by the carrier arranged on the side facing the radiation source, while portions of the filter beside the aperture are in said path,
(c) a clamp circuit is provided, which is connected to clamp the detector signal to a baseline, during the reference window and during the measuring window always until shortly before the reference time interval and measuring time interval, respectively.

9. Bi-frequency infrared spectrometer as set forth in claim 8, characterized in that the filter device comprises a disc rotating about an axis of rotations and having two apertures centrosymmetrical with respect to the axis of rotation, and the apertures are covered on the side of the detector by one filter each, which extends laterally beyond the aperture.

10. Bi-frequency infrared spectrometer as claimed in claim 9, characterized in that
(a) each aperture is an arcuate slot curved about the axis of rotation and
(b) each filter is a substantially semicircular filter plate, which is attached to the disc and has a substantially straight edge along a diameter, the edge of one filter being closely adjacent the edge of the other filter.

11. Bi-frequency infrared spectrometer as claimed in claim 10, characterized in that the disc has a projecting collar on the side facing the detector and concentric to the axis of rotation, the two semicircular filter plates, which together form a full circle, being centered in this projecting collar.

12. Bi-frequency infrared spectrometer as claimed in claim 8, characterized in that
(a) the clamp circuit comprises a capacitor through which the output of the detector or of a filter, to which the output of the detector is applied, is applied to the non-inverting input of a first operational amplifier acting as impedance transformer, the output of this operational amplifier being connected to the inverting input,
(b) the output of the first operational amplifier is applied through a resistor to the inverting input of a second operational amplifier, the output of which is connected to the inverting input through a further resistor and the non-inverting input of which is grounded, whereby the signal received from the first operational amplifier is amplified, and
(c) the output of the second operational amplifier is connected to the input of the first operational amplifier through a switch, which is controlled by a programmer, and a resistor,
closing of the switch causing the capacitor to be re-charged by the amplified voltage from the second operational amplifier, until the voltage at the first operational amplifier becomes zero, the output signal of the clamp circuit being tapped from the output of the second operational amplifier.

13. Signal evaluation circuit for a measuring instrument for measuring the extinction of a sample, wherein a beam emanating from a light source is passed through the sample onto a detector, and two filters having different spectral transmissivities are arranged to be moved alternatingly into the path of the beam, comprising:
a resettable integrator to which the detector signal is applied, synchronized with the filter assembly, during a measuring time interval and during a reference time interval,
a logarithm former to which the output signal from the integrator is applied,
a first and a second memory circuit arranged to receive the output signal from the logarithm former, and
a programmer which provides control signals operative to apply the detector signals to the integrator during the reference and measuring time intervals, to transfer the output signal from the logarithm former to the first and second memory circuits after each reference and measuring time interval, respectively, and subsequently to reset the integrator, and
a differential amplifier, which receives the signals stored in the memory circuits and provides an output signal,
characterized in that
(a) an adjustable corrective voltage is superposed on the detector signal at the input of the integrator during the reference and the measuring time intervals, respectively,
(b) the detector signal is applied to the input of the integrator through two different resistances controlled by a controlled switch,
(c) at least one of the above mentioned resistances is adjustable, and
(d) the controlled switch is controlled by the programmer such that one resistance is effective during the reference time interval and the other resistance is effective during the measuring time interval,
the corrective voltage and the adjustable resistance being adjusted such that a substantially linear relation exists between output signal and concentration taking into account the radiation of components of the instrument itself and the different transmissivities of the filters as well as deviations of the extinction from Beer's Law.

* * * * *